(12) United States Patent
Hill et al.

(10) Patent No.: US 9,441,996 B2
(45) Date of Patent: Sep. 13, 2016

(54) PHASE DETECTION IN MULTI-PHASE FLUIDS

(71) Applicant: Waters Technologies Corporation, Milford, MA (US)

(72) Inventors: Ryan Hill, Watertown, MA (US);
Joshua A. Shreve, Franklin, MA (US);
Robert Dumas, Upton, MA (US);
Sylvain Cormier, Mendon, MA (US);
Edwin Denecke, North Attleboro, MA (US); Kenneth R. Plant, Leominster, MA (US); Kurt D. Joudrey, Chelmsford, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 46 days.

(21) Appl. No.: 14/511,636

(22) Filed: Oct. 10, 2014

(65) Prior Publication Data

US 2015/0101419 A1   Apr. 16, 2015

Related U.S. Application Data

(60) Provisional application No. 61/889,716, filed on Oct. 11, 2013.

(51) Int. Cl.

| | | |
|---|---|---|
| *G01N 21/00* | (2006.01) | |
| *G01J 3/00* | (2006.01) | |
| *G01N 21/55* | (2014.01) | |
| *G01F 1/74* | (2006.01) | |
| *G01N 21/41* | (2006.01) | |
| *G01N 30/74* | (2006.01) | |

(52) U.S. Cl.
CPC .................. *G01F 1/74* (2013.01); *G01N 21/41* (2013.01); *G01N 30/74* (2013.01)

(58) Field of Classification Search
CPC ........ G01N 21/00; G01N 21/55; G01N 1/10; G01J 3/00
USPC .................. 356/72, 300–445, 246; 210/198.2
See application file for complete search history.

(56) References Cited

U.S. PATENT DOCUMENTS

| | | |
|---|---|---|
| 5,672,887 A | 9/1997 | Shaw et al. |
| 7,596,988 B2 | 10/2009 | Usowicz et al. |
| 2005/0213088 A1* | 9/2005 | Brewer .................. G01N 21/05 356/246 |
| 2006/0132770 A1* | 6/2006 | Girvin ................ G01N 15/1459 356/338 |

(Continued)

FOREIGN PATENT DOCUMENTS

| | | |
|---|---|---|
| DE | 228071 A1 | 10/1985 |
| EP | 0121848 A2 | 10/1984 |

(Continued)

OTHER PUBLICATIONS

United Kingdom Search Report; Application No. GB1417862.8; dated Feb. 26, 2015.

*Primary Examiner* — Jewel V Thompson
(74) *Attorney, Agent, or Firm* — McCarter & English, LLP; Deborah M. Vernon

(57) ABSTRACT

The present disclosure relates to phase detection in multi-phase fluids where two fluid phases can be present in the fluid. Phase detection apparatus and methods are disclosed for determining the phase(s) (e.g., supercritical, liquid, and/or gas) of a fluid in a multi-phase fluid system, such as carbon dioxide based separation and chromatography system.

18 Claims, 10 Drawing Sheets

(56) References Cited

U.S. PATENT DOCUMENTS

| | | |
|---|---|---|
| 2007/0059589 A1 | 3/2007 | Arasawa |
| 2007/0103681 A1* | 5/2007 | Hull .................. G01N 21/05 356/317 |
| 2012/0097026 A1 | 4/2012 | Almeida et al. |
| 2015/0260693 A1* | 9/2015 | DeMarco ............. G01N 30/26 356/72 |

FOREIGN PATENT DOCUMENTS

| | | |
|---|---|---|
| EP | 0289833 A2 | 11/1988 |
| EP | 0337173 A2 | 10/1989 |

* cited by examiner

Cross Section Through Optical Path

| n(test) | SFC(Ray) | Test # s | Test/n=1 |
|---|---|---|---|
| 1.00 | 1.00 | 3.07 | 1.00 |
| 1.32 | 3.30 | 7.90 | 2.57 |
| None | 3.38 | 8.05 | 2.62 |

$$Contrast = \frac{Value(n) - Value(n = 1)}{Value(n = 1)}$$

Example Method

PHASE DETECTION IN MULTI-PHASE FLUIDS

CROSS-REFERENCE TO RELATED APPLICATIONS

This application claims priority to U.S. Provisional Application No. 61/889,716 filed Oct. 11, 2013, which is incorporated herein by reference in its entirety.

FIELD OF THE TECHNOLOGY

The present disclosure relates to phase detection in multi-phase fluids, where at least two fluid phases can be present in the fluid. The present disclosure relates more particularly to phase detection apparatuses and methods for determining the phase(s) (e.g. supercritical, liquid, and/or gas) of a fluid in a multi-phase fluid system, such as a carbon dioxide based separation or other chromatography systems.

BACKGROUND

Both carbon dioxide-based chromatography as well as some forms of supercritical fluid chromatography (SFC) use carbon dioxide as the mobile phase. Generally, it is desirable to keep the carbon dioxide condensed (e.g., liquid, at or near a supercritical state) throughout a separation. To maintain the desired state, the carbon dioxide is usually held under elevated conditions (e.g., elevated pressure). Carbon dioxide can change phase from supercritical or liquid to gas within such systems when the elevated conditions are not maintained.

A change in state can occur, for example, in a system designed to receive carbon dioxide from a tank and/or in a system subject to adiabatic heating or other heat transfer. When the carbon dioxide content of the tank is low, the tank cannot apply an adequate elevated pressure to maintain the carbon dioxide in the tank, or delivered to the system, in the desired state. Likewise, adiabatic heating of carbon dioxide during pumping or transport of the pressurized fluid in the system can also lead to phase changes. For example, supercritical/liquid carbon dioxide can undergo a phase transition to a gas or vapor state as a consequence of heat transfer from a pump head to the carbon dioxide mobile phase.

Changes in phase during a chromatographic and/or preparative chromatographic separation can lead to operational errors and/or undesirable outcomes such as irreproducibility, failed separation, peak distortion, and interfering noisy baseline signals.

SUMMARY

The present disclosure relates to methods and phase detection systems that are capable of on-line monitoring of the state of a fluid in a chromatographic and/or separation system, for example condensed carbon dioxide in a carbon dioxide based chromatographic system (i.e., a chromatographic system using carbon dioxide, at least in part, as a mobile phase). In various aspects and embodiments, the phase detection systems can be used to detect and determine the phase, e.g. supercritical, liquid, or gaseous state, of a mobile phase A change in the state of a liquid or supercritical mobile phase to a gaseous state within a system during a chromatographic or separation process can cause operational errors, or even be detrimental. These errors are often not readily indicative of the presence of gas in a mobile phase (e.g., carbon dioxide gas bubbles). On-line or continuous monitoring of the state of the mobile phase delivered to and maintained in a chromatography system (i.e., at a predetermined location within the system) would be beneficial. A phase detection system that can monitor and determine the state of the mobile phase (e.g., carbon dioxide) can allow a user to easily and readily identify the presence of gas in the mobile phase, the source of the error (e.g., a near empty tank, adiabatic heating, or other heat source) and, in some embodiments, correct the problem.

Leak sensors for use with chromatographic systems are known. For example, a device for detecting a condition in a fluid system is described in U.S. Pat. No. 7,596,988 entitled "High Performance Liquid Chromatography Sample Introduction Optimized with Bubble Detection." Some embodiments described therein utilize a light emitter and a light receptor that are sensitive to detect fluid in either the gaseous or liquid state.

Such leak sensors, however, are not applicable to on-line monitoring of the delivery and maintaining of condensed phase (e.g., liquid) carbon dioxide in a high pressure chromatography system. The sensors, when used outside their intended applications, can be fragile, temporary and not sufficiently sensitive to determine variable or frequent phase changes in SFC-type or $CO_2$-based chromatography systems. They are also not designed for or immediately applicable to integrated, on-line, continuous use under SFC-type or $CO_2$-based chromatography conditions.

In one aspect, embodiments of the present disclosure relate to an apparatus for detecting the phase of a fluid including a conduit defining a fluid flow path, a circuit having an optical radiation source and a photo detector, and a housing fixing the relative position of the conduit and the circuit. The housing includes a first aperture adjacent to the optical radiation source and a second aperture adjacent to the photo detector. The first aperture is sized and shaped to filter optical radiation from the optical radiation source to the fluid flow path. The second aperture is sized and shaped to filter the optical radiation from the fluid flow path to the photo detector. The circuit measures the refractive index of a fluid in the fluid flow path, and thereby determines the phase of the fluid.

In another aspect, embodiments of the present disclosure relate to a separation system including a fluid flow source, a separation device in fluid communication with the fluid flow source, and a phase detection apparatus for detecting the phase of the fluid in at least one region of the separation system. The phase detection apparatus has a conduit defining a fluid flow path, a circuit having an optical radiation source and a photo detector, and a housing fixing the relative position of the conduit and the circuit. The housing includes a first aperture adjacent to the optical radiation source and a second aperture adjacent to the photo detector. The first aperture is sized and shaped to filter optical radiation from the optical radiation source to the fluid flow path. The second aperture is sized and shaped to filter the optical radiation from the fluid flow path to the photo detector. The circuit measures the refractive index of a fluid in the fluid flow path, and thereby determining the phase of the fluid.

In a further aspect, embodiments of the present disclosure relate to a method for detecting the phase of a fluid in a separation system. The method includes flowing a fluid through a conduit defining a fluid flow path. The conduit is fixed in a position relative to a circuit having an optical radiation source and a photo detector by a housing defining a first aperture and a second aperture. The method also includes directing optical radiation from the optical radiation source through the first aperture onto the fluid flow path, and directing the optical radiation from the fluid flow path through the second aperture onto the photo detector. The method also includes measuring the refractive index of a fluid in the fluid flow path, and thereby determining the phase of the fluid.

Embodiments described above can further include any one or more of the following features. The apparatus can further have a controller capable of modulating a variable (e.g., pressure) affecting the physical state of the fluid (e.g., bias to a liquid state) based on the fluid phase detected. The housing can flexibly fix the position of the conduit and circuit, and prevent rotation of the conduit, to prevent damage to detector. The conduit can be substantially transparent to optical radiation, e.g., comprise quartz. Similarly, the housing can be substantially opaque to the optical radiation. The light source and the photo detector can be an IR diode and a phototransistor, respectively. The light source aperture can be configured to prevent radiation not incident on the center of the fluid flow path from reaching the conduit. The photo detector aperture can be configured to prevent radiation that does not pass through the center of the fluid flow from reaching the photo detector.

In one or more embodiments, the detector determines the phase change between a first state (e.g., a gas, a mixed gas-liquid, a liquid, or a supercritical fluid) and a second state (e.g., a gas, a mixed gas-liquid, a liquid, or a supercritical fluid) which is different from the first state (e.g., first state a gas, second state a liquid). In particular embodiments, the circuit in the detector provides a signal change of over 1V when a change in state (e.g., change between gas and mixed gas-liquid) occurs.

Separation devices for use with the detector described herein can include any separation device using a mobile phase that can experience a phase change (e.g., from a liquid to a gas) including carbon dioxide based chromatographic systems and a carbon dioxide based extraction systems. In some embodiments, the separation device can be operated at or near supercritical conditions. In some embodiments, the phase detector can be disposed either upstream or downstream of the separation device. In some embodiments, the mobile phase includes, at least in part, carbon dioxide. In some embodiments, the mobile phase is a fluid having a phase change between or transitioning between two states under the full range of possible operation conditions for the chromatography or extraction device.

The apparatus, systems, and methods of the present disclosure offers several advantages over the prior art. For example, some embodiments feature the use of a low volume union and corresponding fittings to minimize fluid flow disruption. Certain embodiments feature advantageous integration of a phase detector device, which can allow one or more of the ability to constantly monitor a fluid system, the ability to operate at high pressures, such as those applicable to a $CO_2$-based chromatography system, and, in some embodiments, an anti-rotation design which stabilizes the detector and reduces even small torsional loads. A further advantage included in some embodiments includes the use of optimized electronics for improved signal to noise ratios.

BRIEF DESCRIPTION OF THE DRAWINGS

The features and advantages of the present disclosure will be more fully understood from the following description of exemplary embodiments when read together with the accompanying drawings, in which.

DETAILED DESCRIPTION

Figure 1:
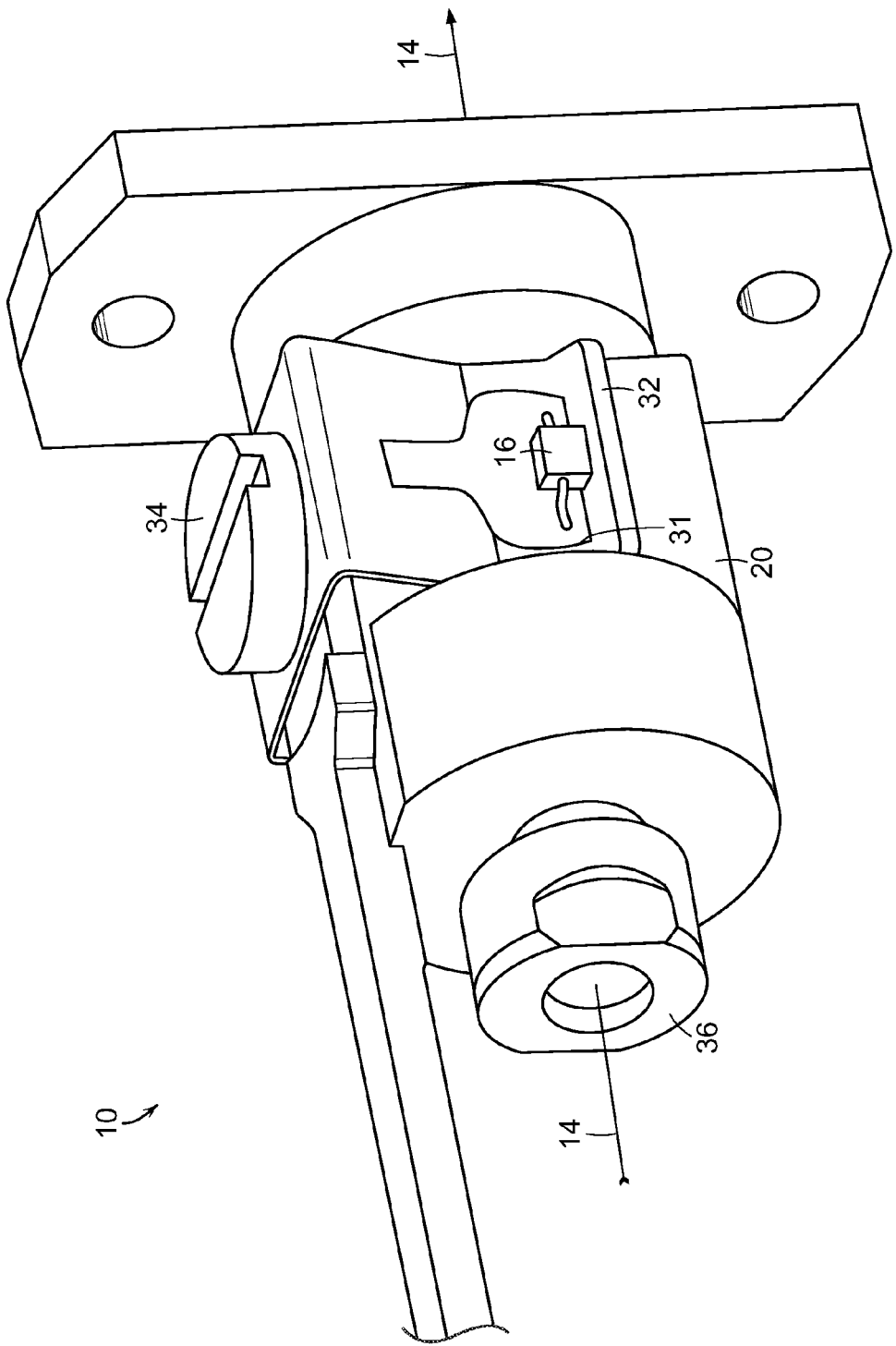
FIG. 1 is a schematic view of an exemplary arrangement of the detector assembly.

The present disclosure relates to a phase detection system applicable to pressurized multi-phase fluid systems, such as a chromatographic, separation, or cooling system. The present disclosure also relates to methods of use thereof. The detection system is capable of identifying the thermodynamic state of a fluid within a separation or chromatographic system without disruption of the flow path. As a result, the thermodynamic state of the fluid in the flow path (e.g. carbon dioxide, carbon dioxide and a modifier, additive and/or sample) can be ascertained on-line and throughout use of the multi-phase fluid system. And, in some cases, adjustment to operating conditions can be made to address the thermodynamic state of the mobile phase (e.g. to keep the system operating under the desired parameters).

As used herein, the term "phase" refers to the thermodynamic state of the fluid, e.g. liquid, gas, or supercritical. A fluid in a system in accordance with the present disclosure may contain more than one phase, for example the fluid can include a liquid phase and a gas phase (i.e., a "mixed gas-liquid phase").

As used herein, the term "multi-phase fluid systems" refers to a system having a fluid capable of liquid/gas transitions within the system. Multi-phase fluid systems can include separations system, chromatographic systems (e.g. SFC, $CO_2$-based chromatography) and cooling systems.

The phase detection system of the present disclosure has several advantages over the prior art. Some of these advantages include the use of standard fittings which do not disturb the fluid flow. The standard fittings, e.g. v-detail fittings, can be used on both ends of the detector assembly. These fittings can effectively act as a union and reduce disruption to fluid flow. As a result, the phase detection system can be used during operation of the attached multi-phase fluid system (e.g., during separation, during extraction) to detect and possibly modify the state of the mobile phase within the system (e.g., apply correct system settings to obtain desired phase state of $CO_2$ during a separation).

Another advantage of the technology of the present disclosure is improved integration within a system, which in turn allows for new applications of the phase detection system. For example, some embodiments feature a housing which robustly connects the detection system to the multi-phase fluid system. The housing allows for secure and easy placement (integration) of the detection system to any portion of the multi-phase fluid system. In addition, the housing serves as a filter to pass and direct light through the fluid and into a light detection device. As a result of this improved integration, the detection system can be used throughout a run to detect and determine if and/or when a phase change occurs. This phase detection information can be used, in some embodiments, to update operating conditions to correct or prevent the phase change.

The detection system is designed to incorporate a seal rated for extended use at high pressures and/or temperatures. A seal rated for extended use at high pressures and/or temperatures is one that can function properly (e.g. maintain a seal) during operation of a system at high pressures or/and extended temperatures. The time associated with extended use can be up to and including the time a normal seal would function properly under normal conditions. The seal design can be rated for use with pressures up to and over 200 psi, 400 psi, 600 psi, 800 psi, 1,000 psi, 1,200 psi, 1,400 psi, 1,600 psi, 1,800 psi, 2,000 psi, 2,500 psi, 3,000 psi, 3,500 psi, 4,000 psi, 4,500 psi and 5,000 psi, which can allow pressurized liquid or gaseous carbon dioxide to be observed. These values can also define a range of pressure values, such as between about 1,600 psi and about 2,500 psi. The seal design can be rated for use with temperatures up to and over 20° C., 40° C., 60° C., 80° C., 100° C., 120° C., 140° C., 160° C., 180° C. and 200° C. These values can also define a range of temperature values, such as between about 80° C. and about 200° C.

The detection system is also designed to minimize or eliminate rotation associated with the detector's fluid conduit, e.g., quartz tube as shown in the illustrative examples (where other tube materials, for example sapphire or mineral crystal, are possible). Extraneous or undesired movement or rotation of the detection system can exert torsional loads on the conduit which can cause the material to fracture. Anti-rotation features (e.g., asymmetric configurations) of the detection system can ensure axial loading of the tube.

In one or more embodiments, an optimized electrical circuit is used which is capable of delivering a clear signal change of over one (1) volt when the phase changes between gas to liquid (or supercritical, or a mixed phase). In some embodiments, resistors utilized in the circuit were selected to provide an optimize signal in response to detection of liquid $CO_2$. In some embodiments, resistors utilized in the circuit were selected to provide an optimize signal in response to detection of gaseous $CO_2$.

FIGS. 1-5 illustrate an exemplary embodiment of the present technology, which relates an apparatus (10) for detecting the phase of a fluid. The apparatus (10) includes a conduit (12) defining a fluid flow path (14); a circuit having an optical radiation source (16) and a photo detector (18); and a housing (20) fixing the relative position of the conduit (12) and the circuit. The housing (20) has a first aperture (22) adjacent to the optical radiation source (16) and a second aperture (24) adjacent to the photo detector (18), wherein the first aperture (22) is sized and shaped to filter optical radiation (26) from the optical radiation source (16) to the fluid flow path (14), wherein the second aperture (24) is sized and shaped to filter the optical radiation (28) from the fluid flow path (14) to the photo detector (18). The circuit of the apparatus (10) measures the refractive index of a fluid in the fluid flow path (14), thereby determining the phase of the fluid.

The fluid systems for which the phase detection system is applicable to can include essentially any closed system using a fluid under controlled pressure and/or temperature. The fluid can include a single component, such as liquid carbon dioxide in a chromatography system, or can include a mixed component system, such as carbon dioxide/methanol in a chromatography system. Examples of fluids which can be used with the phase detection system include carbon dioxide, carbon dioxide/methanol, carbon dioxide/ethanol, and Freon. In addition, the fluid can be any solvent (i.e., single fluid or mixture of two or more fluids) that can experience a phase change between liquid and gas at or near the particular fluid system's operating conditions.

Closed systems containing a fluid under elevated conditions, e.g., controlled pressure and/or temperature, can be susceptible to changes in the fluid conditions wherein the fluid can change phases, such as from liquid to gas. The pressures of the closed system containing the fluid can range from about 25 psi to about 5,000 psi. More preferably, from about 100 psi to about 3,000 psi. In some embodiments, the pressure of the fluid does not exceed 200 psi, 400 psi, 600 psi, 800 psi, 1,000 psi, 1,200 psi, 1,400 psi, 1,600 psi, 1,800 psi, 2,000 psi, 2,500 psi, 3,000 psi, 3,500 psi, 4,000 psi, 4,500 psi and 5,000 psi. These values can also define a range of pressure values, such as between about 1,000 psi and about 2,000 psi. In some carbon dioxide based chromatography system, the pressures of the fluid can range from about 100 psi to about 3,000 psi units. In some embodiments, the pressure does not exceed about 2,000 psi. The operating temperatures in carbon dioxide based chromatography be equal or greater than 20° C., 40° C., 60° C., 80° C., 100° C., 120° C., 140° C., 160° C., 180° C. and 200° C. These values can also define a range of temperature values, such as between about 80° C. and about 200° C. In some embodiments, the temperature can range between about 5° C. and about 50° C., or between about 15° C. and about 38° C.

The conduit (12) defining a fluid flow path (14) can be any pipe or tube that carries or transports fluid that is under controlled pressure or temperature from one location to another location. Preferably, the conduit (12) is, or can be made, substantially transparent to optical radiation. The conduit (12) can be any device defining a fluid flow path (14), or passage, made using a material transparent to optical radiation that is compatible with a separation or chromatographic system, such as a carbon dioxide based chromatographic system, such as any chromatography system designed for use with a mobile phase containing $CO_2$ and available from Waters Technologies Corporation, Milford, Mass. Preferably, the conduit (12) is made of quartz. However, other optically transparent materials can be used as well, such as, for example, optically transparent glass, acrylic glass (e.g., Lucite), or transparent forms of corundum. The conduit (12) can have an internal diameter (i.d.) that is applicable for transporting fluids in the particular fluid system. Preferably, the internal diameter of the conduit should be similar to the internal diameter of the tubing transporting the fluid in the system and to the conduit. A mis-match of internal diameters between the conduit and the tubing can result in a pressure change in the conduit that is not representative of the fluid in the system. For example, if an SFC system using carbon dioxide as the mobile phase uses 0.03 inch i.d. tubing to transport liquid carbon dioxide and the detection system uses a 0.01 inch i.d. conduit, then the smaller conduit internal diameter can cause the carbon dioxide to experience a local increase in pressure in the conduit that is not representative of the system and cannot detect a phase change present in the system. Likewise, if an SFC system uses 0.007 inch i.d. tubing to transport liquid carbon dioxide and the detection system uses a 0.02 inch i.d. conduit, then the larger conduit internal diameter can cause the carbon dioxide to experience a local decrease in pressure in the conduit that is not representative of the system and can detect a phase change which is not present in the system. In some embodiments, the difference in i.d. between the conduit and the tubing is less than about 25%, 20%, 15%, 10%, 5%, 2%, or 1%. These values can also define a range of differences, such as between about 2% and about 5%.

Figure 5:
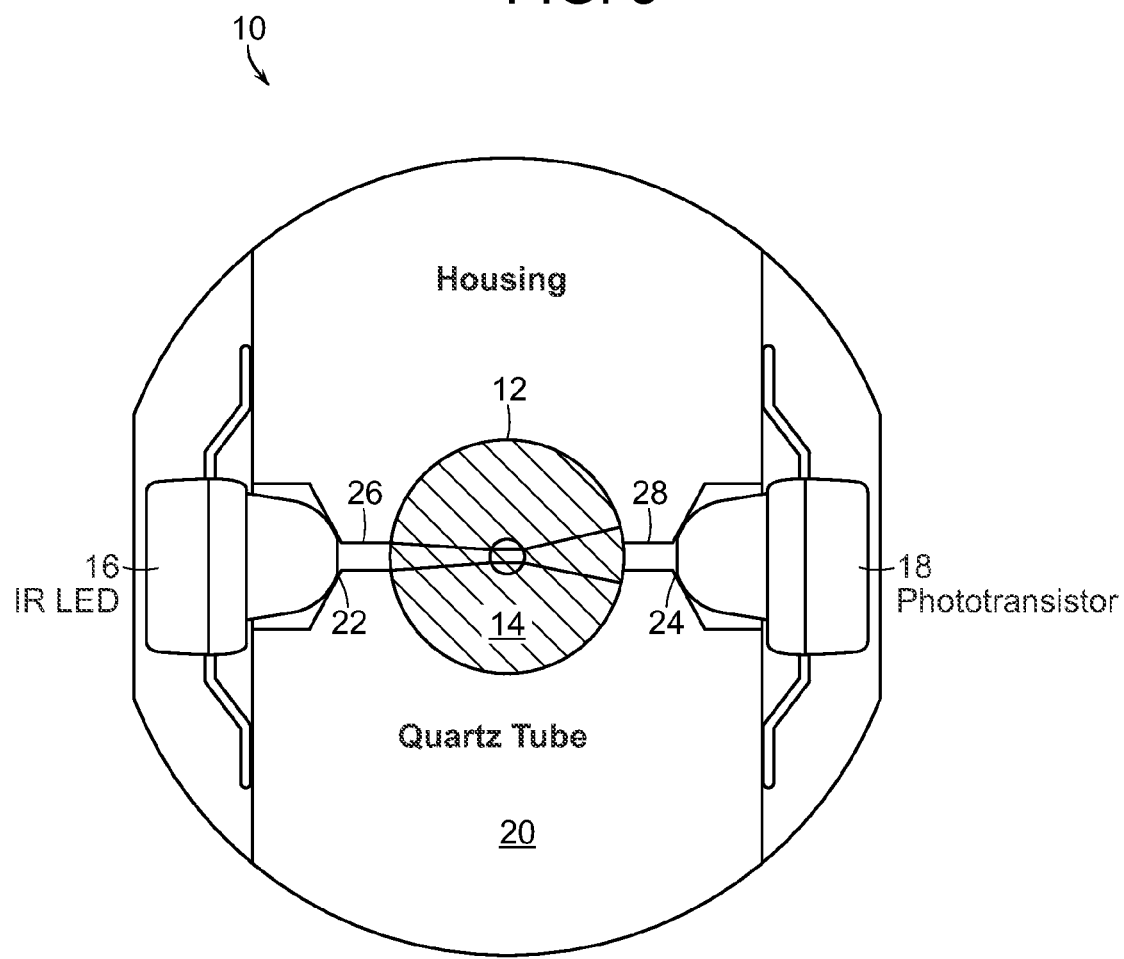
FIG. 5 is a cross-section of an optical path for an exemplary arrangement of the detector.
Figure 7:
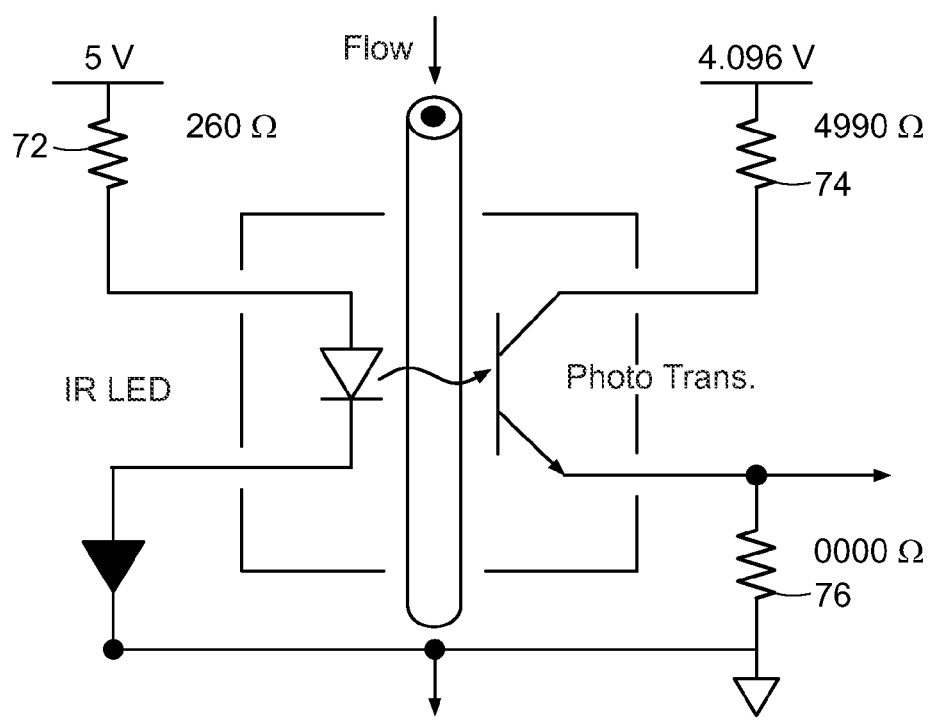
FIG. 7 is a circuit diagram for an exemplary arrangement of the detector.

The circuit includes an optical radiation source (16) and a photo detector (18). FIGS. 5 and 7 show exemplary embodiments of the circuit. The optical radiation source (16) can be any light emitting device. Examples of optical radiation sources includes light emitting diodes, UV/VIS lamps, and lasers. Preferably, the source is an IR light emitting diode (IR LED). The photo detector (18) can also be any photon detecting device capable of converting photons or light into an electrical signal, either current or voltage. Examples of photo detectors include phototransistors and photodiodes. Preferably, the photo detector is a photodiode.

The circuit is capable of delivering a signal change when the phase of the fluid changes between a gas, a liquid, a supercritical or neat supercritical, or a mixed phase. When the phase of the fluid changes (e.g., gas bubble form in a fluid), the refractive index of the fluid flowing past the circuit also changes (e.g., due to the presence of gas bubbles in the fluid flow stream). The change in refractive index changes the diffraction pattern or angle of the light passing through the flow cell and circuit. These changes in light intensity are recorded by the photo detector. In one embodiment, the circuit can include an IR LED optical radiation source and a phototransistor photo detector. The phase change alters the IR throughput and triggers a threshold. A threshold value can be set at any value between a reading for 100% liquid and 100% gas. In some embodiments it is set to half way between a value for 100% liquid and the a value for 100% gas. In general, the IR throughput readings/values would be determined experimentally and would correlate the type of solvent used as the mobile phase fluid. The circuit can be capable of delivering a signal change over 1V when the phase of the fluid changes, for example, between gas and liquid. In some embodiments, resistors in the circuit are selected to have the largest signal to noise properties corresponding to gas and liquid readings without exceeding full scale values of the analog to digital converter. When optimized, the circuit can provide a clear indication of a phase change through a showing of a signal change of or greater than 1 V. In general, the circuit is capable of measuring the refractive index of a fluid in the fluid flow path (14), thereby determining the phase of the fluid (i.e., gas, liquid, at or near supercritical, or a mixture thereof).

For example, the circuit will monitor the fluid and deliver a signal as the fluid passes through the conduit. When the fluid is 100% liquid, e.g. 100% liquid carbon dioxide, the signal is associated with or can be calibrated to 100% transmittance. Upon a change of the fluid phase from 100% liquid to a liquid/gas mix, the signal will be less than 100% transmittance. The concept can be analogously applied to supercritical/liquid and supercritical/gas mixtures. Without being bound by any particular theory, it is believed that one method of operation includes the presence of the gas bubbles in the supercritical/gas mixture causes the light to scatter and less light to reach the detector. The loss of transmittance to the detector can be indicative of a phase change or the presence of multiple/mixed phases.

An exemplary circuit diagram for the circuit is shown in FIG. 7. Resistance values for resistors (72, 74, and 76) are selected to optimize the output range of the signal and to increase the signal to noise ratio. In the embodiment shown in FIG. 7, a resistance of about 260 ohms is provided for resistor (72), a resistance of about 4990 ohms is provided for resistor (74), and about 0 ohms is selected for resistor (76) (e.g., no resistor is provided in this location). In another embodiment, a resistance of about 681 ohms is provided for resistor (72); about 332 ohms is provided for resistor (74); and about 221 ohms is provided for resistor (76).

Figure 2:
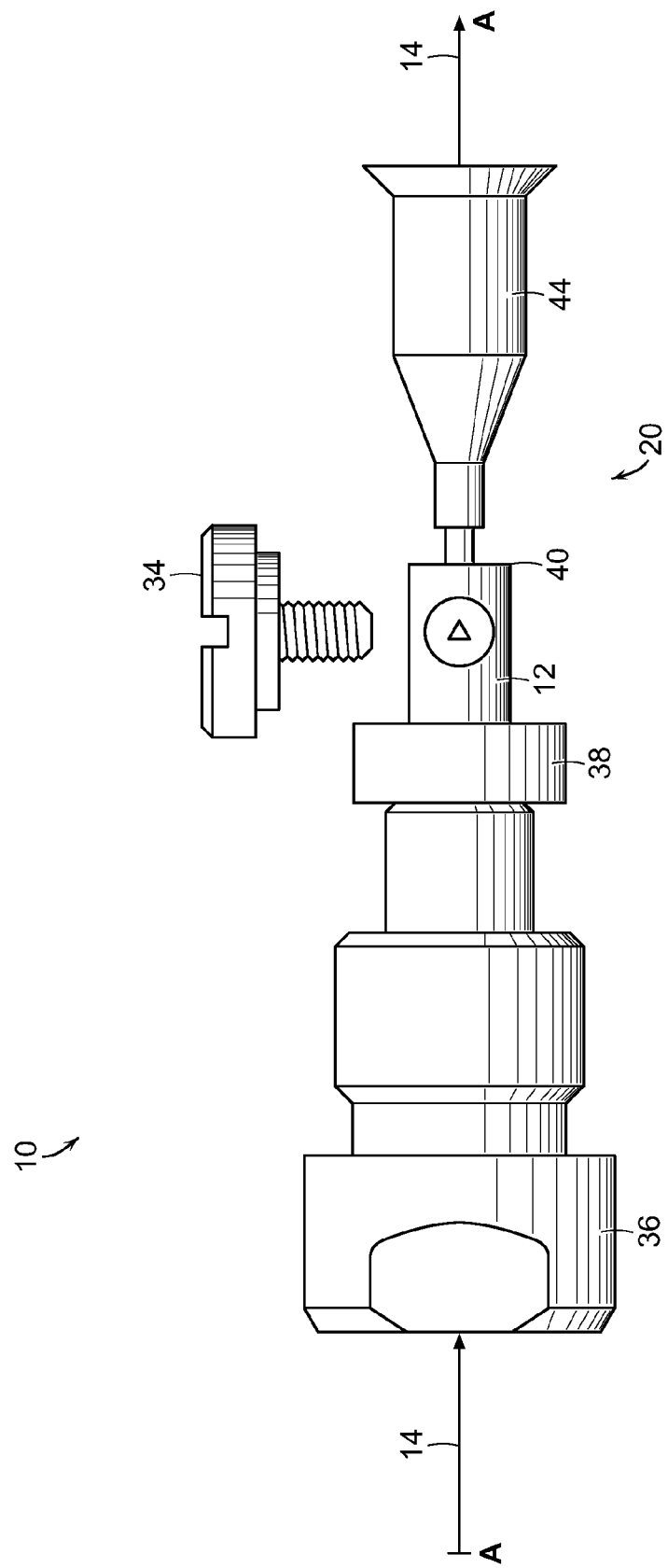
FIG. 2 is a schematic view of a portion of the detector assembly of FIG. 1.
Figure 3:
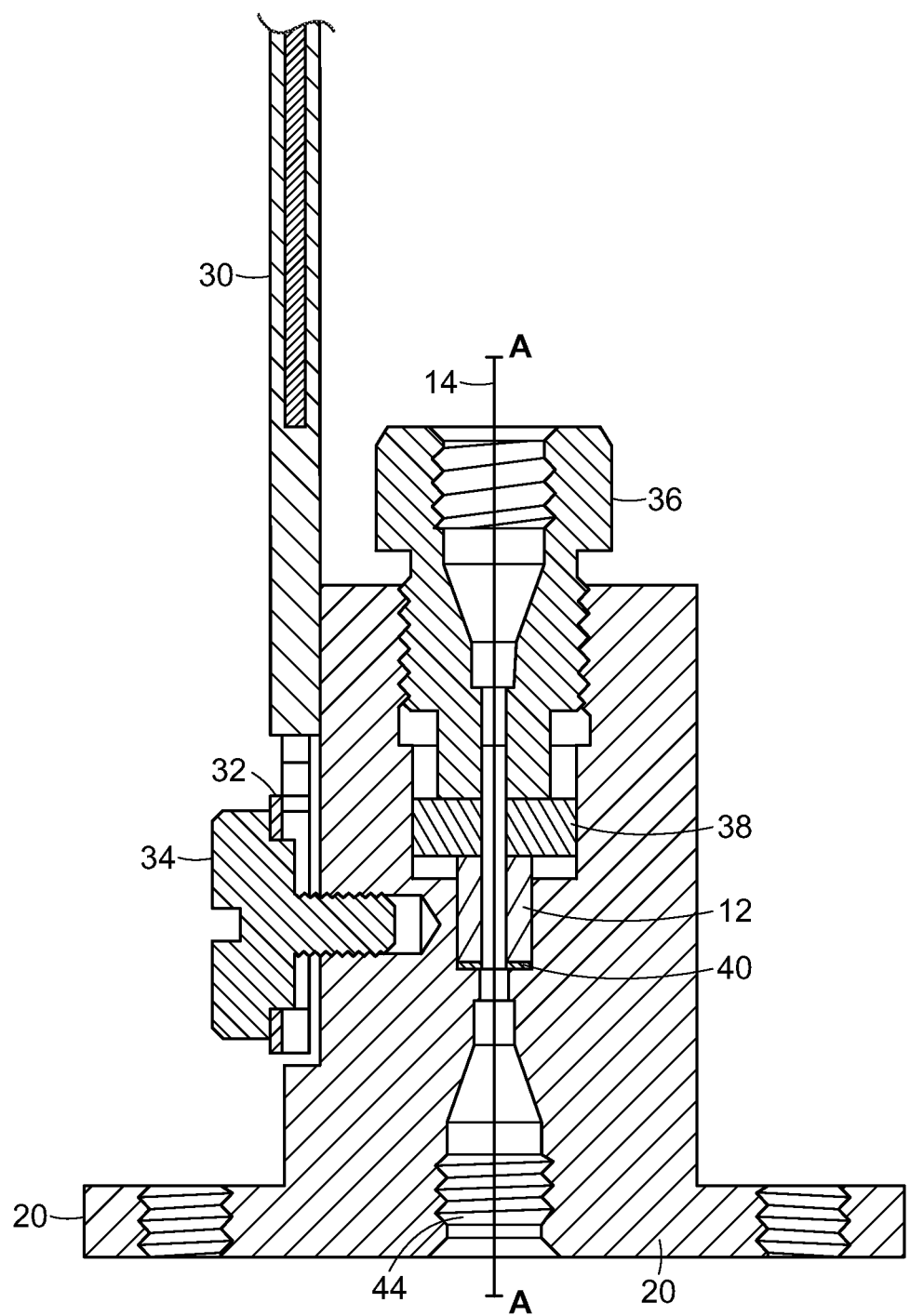
FIG. 3 a cross-sectional schematic view of the detector assembly of FIG. 1.

In one embodiment, the housing (20) fixes the relative position of the conduit (12) and the circuit (e.g., the source (16) and detector (18)), as well as defines the fluid flow path (14). As shown in FIG. 1 with the device (10) assembled, the fluid flow path (14) flows through the housing (20) by entering a channel through fitting retainer (36) and flowing in the direction defined by the interior of the housing (20). Within the housing, fluid flow path (14), as shown in FIGS. 2 and 3, extends along line A-A from fitting retainer (36), through conduit (12), and out of the detector (10) through a standard v-shaped fitting (44). As both fitting retainer (36) and v-shaped fitting (44) are standard fittings that typically do not substantially add to the dead volume of a system, detector (10) can be placed at any desired location along a fluid path.

Figure 4:
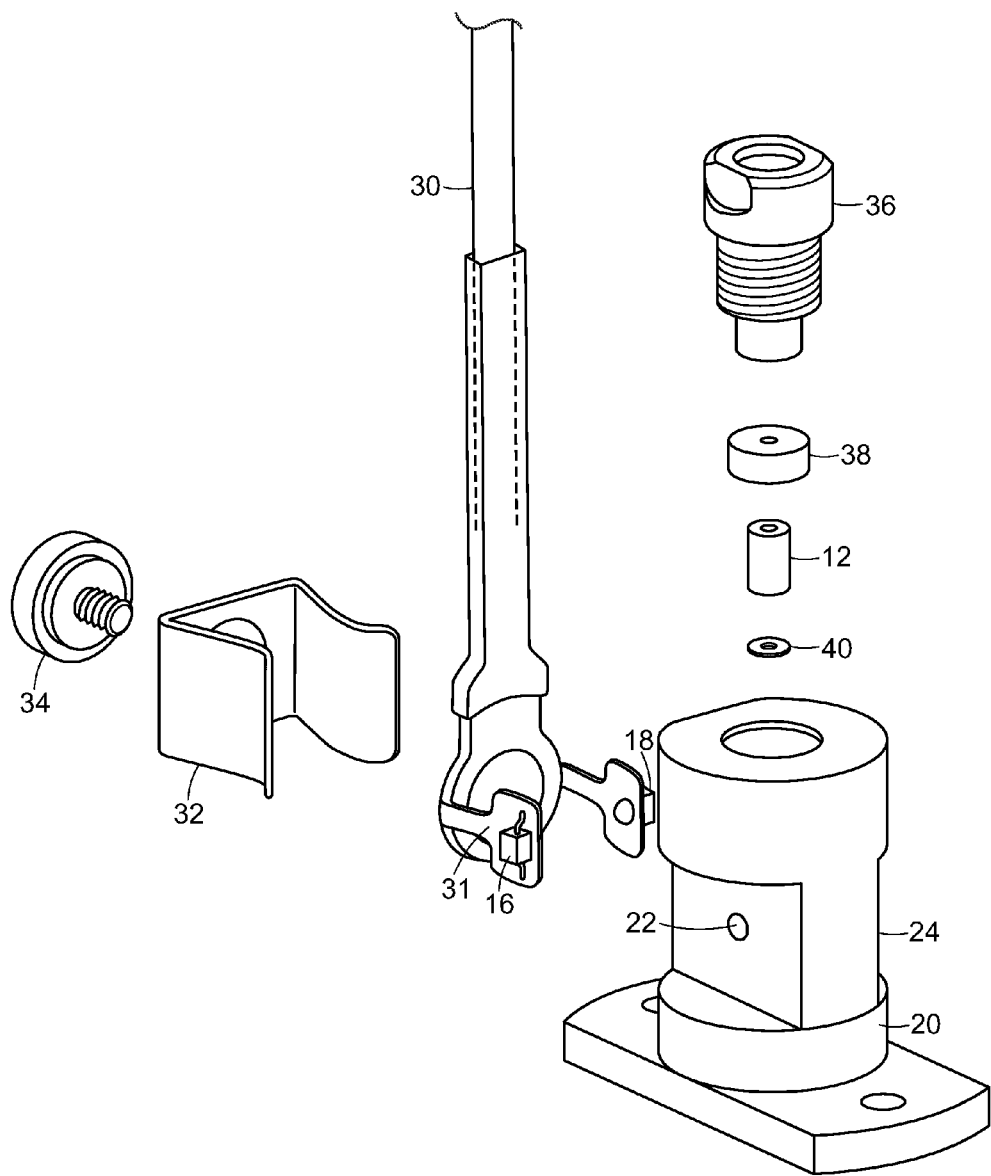
FIG. 4 is an exploded schematic view of the detector assembly of FIG. 1.

The housing (20) includes a first aperture (22) and a second aperture (24) which are offset opposite each other, as shown in FIGS. 4 and 5, and sized to accommodate the optical radiation source (16) and a photo detector (18), respectively. Preferably, the housing is substantially opaque to the optical radiation. The first aperture (22) is adjacent to the optical radiation source (16) and a second aperture (24) is adjacent to the photo detector (18). As shown in FIG. 5, the first aperture (22) is sized and shaped to filter optical radiation (26) from the optical radiation source (16) to the fluid flow path (14). In general, the size of the first aperture (22) is optimized to prevent or minimize stray light (e.g., non-incident light) from entering the fluid flow path (14). Stray light is a constant offset and detracts from a signal operating range. As a result, the first aperture is sized to minimize the stray light, such that the offset is lessen.

Figure 6:
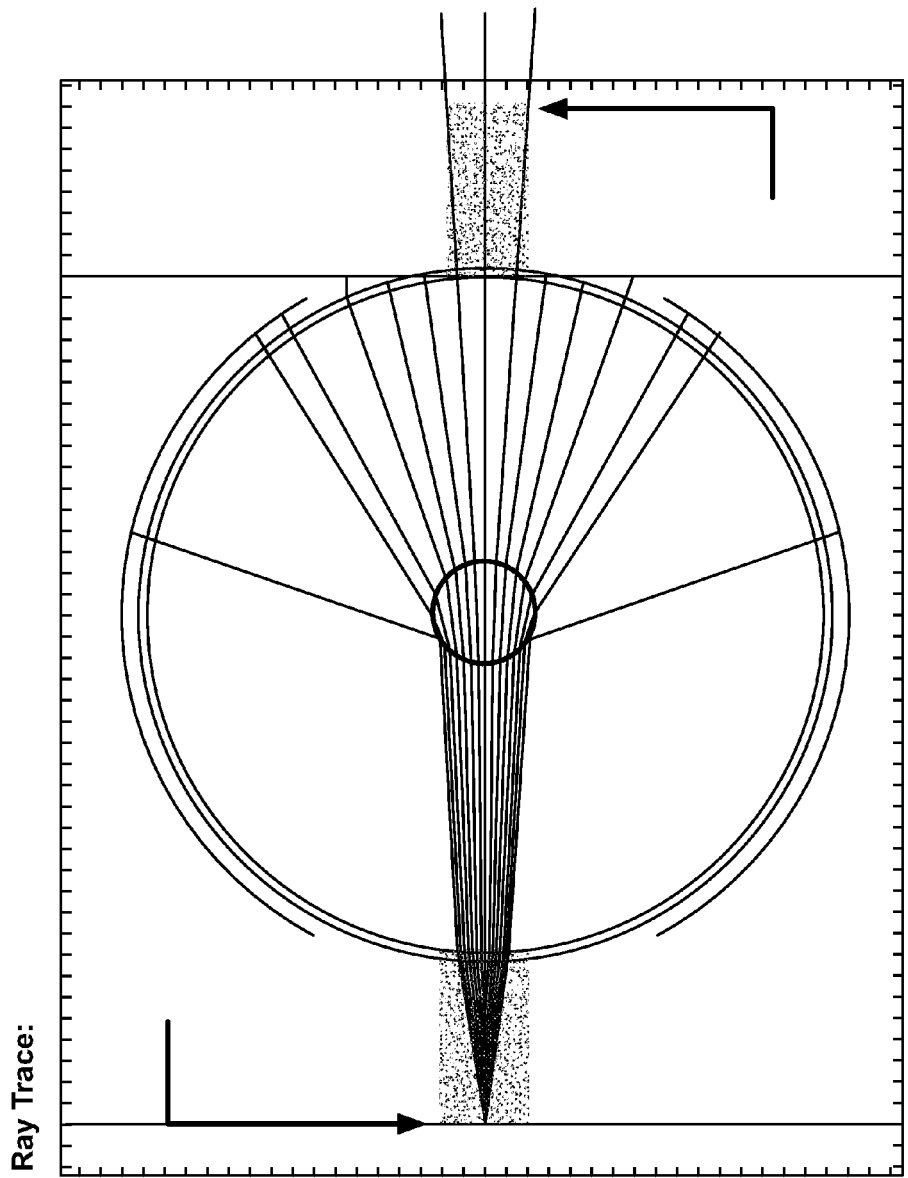
FIG. 6 is an optical ray path for an exemplary arrangement of the detector.

In reference to FIGS. 5 and 6, the first aperture (22) can be configured to prevent optical radiation that is not incident on the center of the fluid flow path (14) from reaching the conduit (12). Similarly, the second aperture (24) can be configured to prevent optical radiation that does not pass through the center of the fluid flow path (14) from reaching the photo detector. In some embodiments, the shape and material type can be selected to apply a light concentrating effect on the fluid with the flow path. For example, the concentrating or focusing effect can be optimized by the relative refractive indexes at material interfaces. By selecting appropriate materials and shape of the conduit (12), one can tailor the relative refractive indexes to achieve the light concentrating effect within the center of the fluid flow path (14). In one embodiment, it the material and shape of the conduit (12) is a quartz tube.

As shown in FIG. 5, the second aperture (24) is sized and shaped to filter optical radiation (28) from the fluid flow path (14) to the photo detector (18). The size of the second aperture (24) can be larger, equal or less than the size of the first aperture (22) depending on the optimization of the dynamic range of the circuit. Typically, the sizes of the apertures are selected such that enough light passes through the second aperture (24) to create a readable signal in detector (18). While it is desirable to have second aperture (24) be large enough to collect as much light traveling through fluid path (14) as possible, at the same time, it is desirable to have second aperture (24) be small enough to block light traveling around the fluid path as possible. If the detector (18) receives extraneous light which does not pass through the fluid, an offset is created thereby limiting the dynamic range of the detector. The shape of the first and second apertures (22 and 24) can independently be any shape that allows for light to pass through. First and second apertures can have the same shape or they may differ. In one embodiment, the shape of both apertures (22 and 24) is circular.

With reference to the exemplary embodiments shown in FIGS. 1, 3 and 4, a cable (30) is connected to the circuit to provide electrical power to the optical radiation source (16) and to carry the signal generated by the photo detector (18) located on arms (31). The optical radiation source (16) and the photo detector (18) are positioned opposite each other and separated apart to fit on opposite sides of the housing bracketing the conduit (12) and fluid flow path (14). The cable is held in place by a retaining clip (32) and a screw (34). These secure the optical radiation source (16) and the photo detector (18) in place and prevent movement that can interfere with the detection system. In some embodiments, rubber pads are placed between arms (31) and retaining clip (32) to allow for a more secure and flexible connection.

A fitting retainer (36) is used to connect detector (10) to a fluidic system with minimal volume added. In FIGS. 1-4, fitting retainer (36) is a V-detail fitting retainer that adds little volume to a system. In addition fitting retainer (36) has an adjustable compression feature to allow for the retention of the components (e.g., conduit (12)) within housing (20). The phase detector apparatus (10) can be integrated, directly or indirectly, between the fluid flow source and the separation device. The use of these fittings on each end of the conduit (12) can be able to minimize disruption of the fluid flow. In addition, by integrating the phase detection device (10) into a system having a flow source and a separation device, the phase detector can operate on-line during a chromatographic separation. That is, fluid does not need to be separated or collected separately. The phase detection device (10) actively monitors the fluid to be used in the separation.

An anti-rotation key (38) is used to inhibit rotation of conduit (12) during phase detection. In the embodiment shown, anti-rotation key (38) is asymmetrically shaped component (e.g., an oval), which after the components within the housing (20) are retained by placement of the fitting retainer (36) limits and/or prevents rotation of the conduit (12). While the embodiments show illustrate key (38) as an oval, other asymmetric configurations are possible. The housing (20) is adapted to accept the anti-rotation key (38) in one or possibly more orientations. However, the positioning of the anti-rotation key (38) within the housing (20), especially after retention by fitting retainer (36) prevents rotation of the conduit, thereby preventing damage to the conduit.

The embodiment shown in FIGS. 3 and 4 features a conduit gasket (40). Conduit gasket (40) is used to seal the conduit (12) from the housing (20). In some embodiments, the gasket is formed of PEEK, PTFE (e.g., Teflon®) or FFKM (Kalrez®). In certain embodiments, the gasket is about 0.005 inches in thickness. The gasket (40) can be thicker or thinner depending on the application and/or implementation. The phase detector apparatus (10) can be integrated between the fluid flow source and the separation device. In certain embodiments, the use of a gasket (40) and fittings (36) allows for use of the conduit and phase detection system up to an operating pressure of at least about 2,000 psi.

In another embodiment, the present disclosure relates to a supercritical (or near supercritical, or liquid) phase separation system including a fluid flow source, a separation device in fluid communication with the fluid flow source, and a phase detection apparatus for detecting the phase of the fluid in at least one region of the separation system, wherein the phase detection apparatus includes a conduit defining a fluid flow path, a circuit including an optical radiation source and a photo detector, and a housing fixing the relative position of the conduit and the circuit, the housing having a first aperture adjacent to the optical radiation source and a second aperture adjacent to the photo detector, wherein the first aperture is sized and shaped to filter optical radiation from the optical radiation source to the fluid flow path, wherein the second aperture is sized and shaped to filter the optical radiation from the fluid flow path to the photo detector, and wherein the circuit measures the refractive index of a fluid in the fluid flow path, thereby determining the phase of the fluid.

The supercritical (or near supercritical, or liquid) phase separation system can include any separation or phase chromatographic system wherein a change in fluid phase can occur. For example, a fluid-based separation system can include a carbon dioxide based chromatographic system or a carbon dioxide based extraction system, both designed to operate, at least in part, in the supercritical or near supercritical range of $CO_2$. The fluid flow source can include any fluid source capable of providing fluid for a separation or chromatographic system. Fluid flow sources can include fluid cylinders or tanks, or a feed from a continuous source, such as a house supply feed. In one embodiment, the fluid-based separation system is a carbon dioxide based chromatographic system comprising a fluid flow source including a tank with a two stage regulator. The separation system can include a pump or pumping system which delivers the fluid as the mobile phase to effect a carbon dioxide based chromatographic separation.

The phase detection apparatus for detecting the phase of the fluid in at least one region of the separation system can include the phase detection system as provided by the present disclosure. The phase detection apparatus can be upstream or downstream of any pump or pumping system associated with the separation device. Additionally, the phase detection apparatus can be disposed upstream of the separation device. Alternatively, the phase detection apparatus can be disposed downstream of the separation device. Some embodiments feature the use of multiple phase detection systems located at different locations within a system (e.g., a first phase detection system located upstream of a separation devices and a second phase detector system located downstream of a separation device.)

The phase detection apparatus can also include a controller in communication with the fluid phase detector. The controller can be capable of modulating at least one variable affecting the physical state of the fluid flow based upon the fluid phase detected by the fluid phase detector. For example, the controller can be able to modulate at least one parameter to bias the fluid flow to the liquid state when the fluid phase detector detects a gas or mixed gas-liquid phase in the fluid flow. The controller can be a servo-controller that upon receipt of information of a phase change actuates a mechanical and/or electrical change in the system to address a variable. The variables which can be modulated to affect the physical state of the fluid flow include pressure and/or temperature. For examples, if the phase detection apparatus detects a phase change in the fluid, the controller can increase the pressure of the fluid system to bias the fluid from a gas state to a liquid state. For example, the pressure applied from a pumping system or pressurization system could be increased. In other embodiments, one or more pressure regulators within the system can be modulated by the controller to increase the pressure. In some embodiments, a back pressure applied to the system could also be modified to address detection of a phase change or near phase change by the controller. In addition, temperature of the system can be modified in response to detection of a phase change or near phase change through known temperature control mechanisms in communication with the controller. The analogous apparatus and method is likewise applicable to supercritical fluids.

The housing of the phase detector apparatus can be capable of flexibly fixing the relative position of the conduit and the circuit. By flexibly fixing these components, damage to the circuit can be prevented while maintaining the relative position of the conduit and the circuit. For example, a "hard" or rigid mounting (e.g. metal mounting) to secure and align the circuit components (16 and 18) to the fluid conduit (12) can result in damage to the fragile and sensitive optics of 16 and 18. In particular, scratching of the components (16 and 18) can result if there is no give or flexibility between the mounting device and the housing (20) enclosing conduit (12). However, to maintain alignment, arms (31) are formed of a plastic, elastomer material, or other such flexible material, to provide a flexible fixing of the conduit and circuit.

Figure 10:
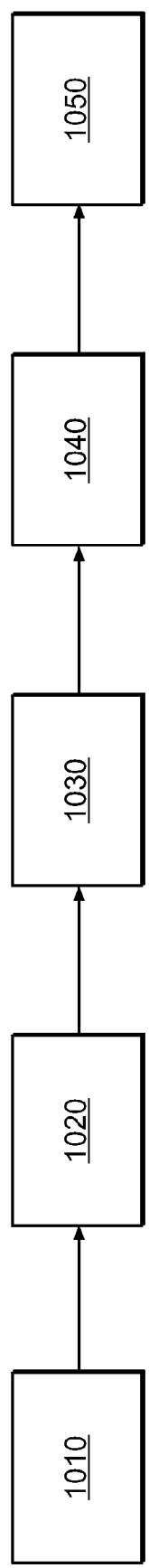
FIG. 10 illustrates a general a method for detecting the phase of a fluid in a separation system according the present invention.

In another embodiment, the present disclosure relates to a method (FIG. 10) for detecting the phase of a fluid in a separation system, including flowing a fluid through a conduit defining a fluid flow path (1010), wherein the conduit is fixed in a position relative to a circuit comprising an optical radiation source and a photo detector by a housing defining a first aperture and a second aperture; directing optical radiation from the optical radiation source through the first aperture onto the fluid flow path (1020); directing the optical radiation from the fluid flow path through the second aperture onto the photo detector (1030); and measuring the refractive index of a fluid in the fluid flow path (1040), thereby determining the phase of the fluid. The method can further include performing liquid/supercritical phase chromatography or separation on a sample in the fluid after determining that the phase of the fluid is supercritical (1050). Alternatively, the method can further include performing a liquid phase chromatography or separation on a sample in the fluid after determining that the phase of the fluid is liquid.

EXAMPLES

Example 1

Bubble Detection Signal Comparison

Figure 8:
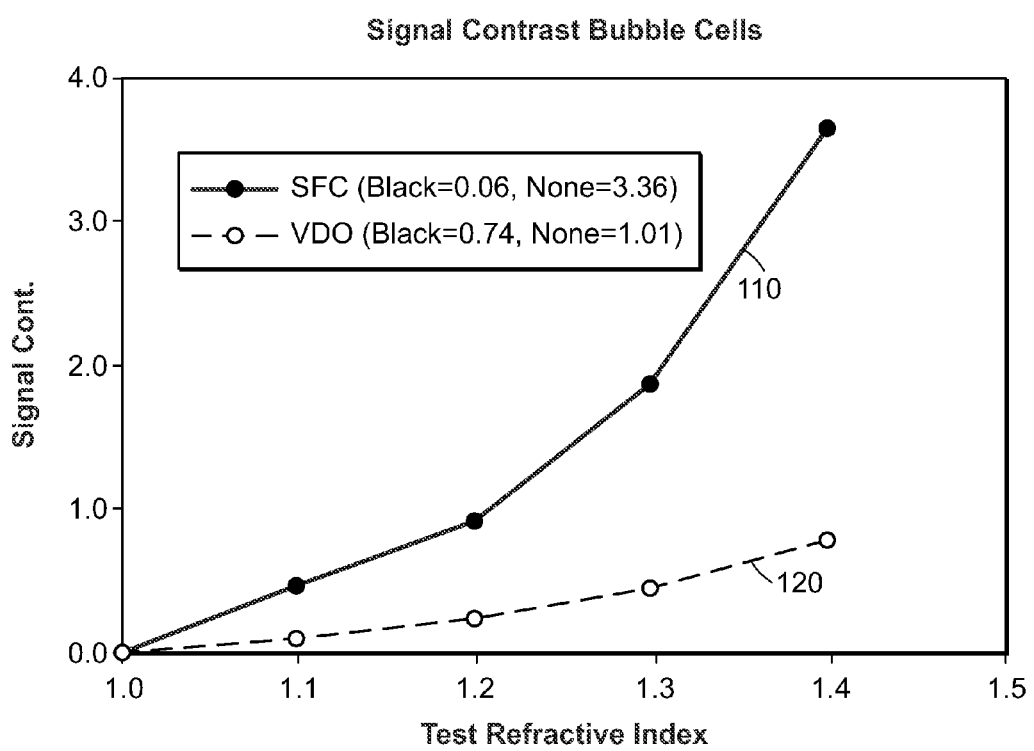
FIG. 8 is a bubble detection signal comparison using an exemplary arrangement of the detector.

To demonstrate the detector's response to a change in phase, a bubble detection signal comparison test was performed. In particular, test solvents with a known refractive index were passed through the detector shown in FIG. 1 to determine a contrast signal detection by the circuit of the detector. In addition, the same test solvents were passed through a leak detector of the type described in U.S. Pat. No. 7,596,988. As shown in FIG. 8, the contrast in detection signal is much greater in the detector of type of the present invention (i.e., labeled SFC and given curve number (110)) than the leak detector of U.S. Pat. No. 7,596,988 (i.e., labeled VDD and given curve number (120)). Both signals were taken with the mechanism described herein. The contrast difference is due, in part, to the circuit. The plot marked VDD uses the standard circuit from the VDD while the SFC line uses an optimized circuit for maximum contrast. As a result of the greater signal contrast provided by the detector of the present technology, finer distinctions between phase changes can be detected and acted upon. Thus, the detector of the present invention can be used to monitor and adjust changes in a variable multi-phase fluidic system, such as a $CO_2$-based chromatography or extraction system.

Example 2

Tank "Running Dry" Simulation

Figure 9:
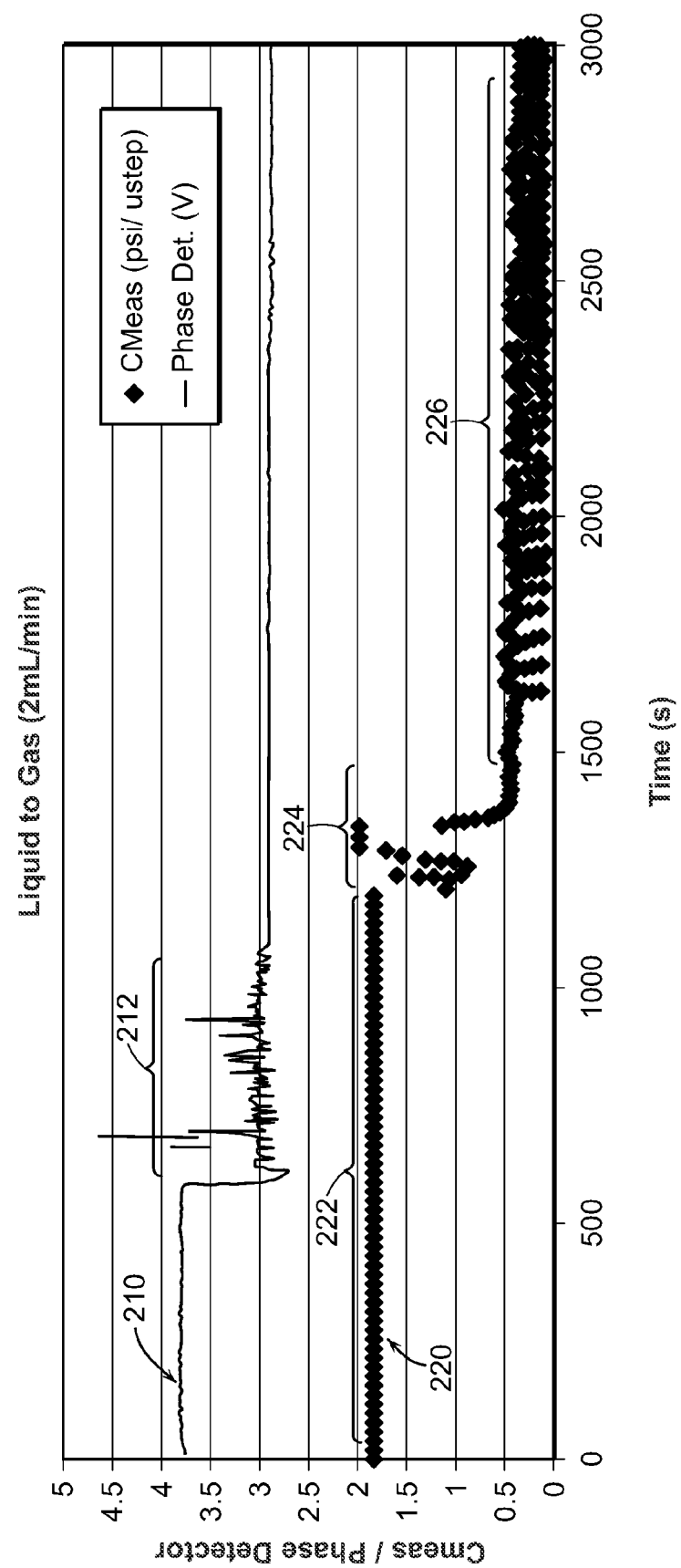
FIG. 9 is a tank "running dry" simulation using an exemplary arrangement of the detector.

To demonstrate detection of a phase change by the detector shown in FIG. 1, a "running dry" simulation test was conducted with a $CO_2$ tank. In this test, the results of which are shown in FIG. 9, a tank including $CO_2$ and configured to deliver the $CO_2$ in a liquid phase was attached to a pump. Between the tank and the pump, the detector of FIG. 1 was positioned. FIG. 9 shows the results of two recorded signals. The first signal, signal (210), is from the phase detection device (10) of FIG. 1. The second signal, signal (220), is taken from the pump and is an internal measurement of the compressibility of a solvent passing through the pump (e.g., $CO_2$ delivered from the tank). The test is conducted by first allowing the system (tank, detector, and pump) to run with the tank open to deliver liquid $CO_2$. The tank is then closed at around 600 seconds. Soon thereafter the solvent ($CO_2$) is known two be present as both a liquid and gas phase. The detector (10), seeing the mixed phase, provided an erratic signal, see portion (212). The pump is able to compress and deliver the $CO_2$ as long as the solvent includes liquid. Signal (220) shows that the pump is function normally, that is, the pump is able to deliver a solvent during portion (222). During portion (224), the pump struggles to deliver as the mixed phase becomes highly gaseous. Thereafter, the pump stops functioning properly in portion (226) as the pump has run out of liquid $CO_2$. This test shows that the detector (10) can see the phase transition occurring as demonstrated by the subsequent malfunction of the pump, located downstream of the detector.

The specification should be understood as disclosing and encompassing all possible permutations and combinations of the described aspects, embodiments, and examples unless the context indicates otherwise. One of ordinary skill in the art will appreciate that the invention can be practiced by other than the summarized and described aspect, embodiments, and examples, which are presented for purposes of illustration, and that the invention is limited only by the following claims.

What is claimed is:

1. An apparatus for detecting the phase of a fluid in a multi-phase fluid system comprising:
    a conduit defining a fluid flow path;
    a circuit comprising an optical radiation source and a photo detector;
    a housing fixing the relative position of the conduit and the circuit, the housing comprising a first aperture adjacent to the optical radiation source and a second aperture adjacent to the photo detector, wherein the first aperture is sized and shaped to filter optical radiation from the optical radiation source to the fluid flow path, wherein the second aperture is sized and shaped to filter the optical radiation from the fluid flow path to the photo detector, and wherein the circuit measures the refractive index of a fluid in the fluid flow path, thereby determining the phase of the fluid; and a controller in communication with the fluid phase detector, the controller being capable of modulating at least one variable affecting the physical state of the fluid flow based upon the fluid phase detected by the fluid phase detector.

2. The apparatus of claim 1, wherein the controller modulates at least one variable affecting the physical state of the fluid flow, to bias the fluid flow to the liquid state, when the fluid phase detector detects a gas or mixed gas-liquid phase in the fluid flow.

3. The apparatus of claim 1, wherein the housing flexibly fixing the relative position of the conduit and the circuit, thereby preventing damage to the circuit while maintaining the relative position of the conduit and the circuit.

4. The apparatus of claim 1, wherein the circuit delivers a signal change when the phase of the fluid changes between a gas, a liquid, or a mixed gas-liquid phase.

5. The apparatus of claim 1, wherein the housing prevents rotation of the conduit, thereby preventing damage to the conduit.

6. The apparatus of claim 1, wherein the conduit is substantially transparent to the optical radiation.

7. The apparatus of claim 1, wherein the fluid comprises $CO_2$.

8. The apparatus of claim 1, wherein the optical radiation source comprises an IR diode and the photo detector comprises a photodiode.

9. The apparatus of claim 1, wherein the first aperture is configured to prevent optical radiation that is not incident on the center of the fluid flow path from reaching the conduit.

10. The apparatus of claim 1, wherein the second aperture is configured to prevent optical radiation that does not pass through the center of the fluid flow path from reaching the photo detector.

11. A separation system comprising:
a fluid flow source, a separation device in fluid communication with the fluid flow source, and a phase detection apparatus for detecting the phase of the fluid in at least one region of the separation system, wherein the phase detection apparatus comprises:
a conduit defining a fluid flow path,
a circuit comprising an optical radiation source and a photo detector, and
a housing fixing the relative position of the conduit and the circuit, the housing comprising a first aperture adjacent to the optical radiation source and a second aperture adjacent to the photo detector, wherein the first aperture is sized and shaped to filter optical radiation from the optical radiation source to the fluid flow path, wherein the second aperture is sized and shaped to filter the optical radiation from the fluid flow path to the photo detector, and wherein the circuit measures the refractive index of a fluid in the fluid flow path, thereby determining the phase of the fluid.

12. The system of claim 11, wherein the phase detection apparatus is disposed upstream of the separation device.

13. The system of claim 11, wherein the phase detection apparatus is disposed downstream of the separation device.

14. The system of claim 11, wherein the separation device comprises supercritical fluid chromatography or supercritical phase extraction.

15. The system of claim 11, wherein the phase detector apparatus is integrated between the fluid flow source and the separation device by fittings on each end of the conduit to minimize disruption of the fluid flow.

16. A method for detecting the phase of a fluid in a separation system, comprising:
flowing a fluid through a conduit defining a fluid flow path, wherein the conduit is fixed in a position relative to a circuit comprising an optical radiation source and a photo detector by a housing defining a first aperture and a second aperture;
directing optical radiation from the optical radiation source through the first aperture onto the fluid flow path;
directing the optical radiation from the fluid flow path through the second aperture onto the photo detector;
measuring the refractive index of a fluid in the fluid flow path, thereby determining the phase of the fluid; and
modulating at least one variable affecting the physical state of the fluid flow, to bias the fluid flow to the liquid state, when the fluid phase detector detects a gas or mixed gas-liquid phase in the fluid flow.

17. The method of claim 16, wherein the fluid comprises $CO_2$.

18. The method of claim 16, further comprising performing a supercritical phase chromatography or separation on a sample.

* * * * *